(12) United States Patent
Yoo et al.

(10) Patent No.: US 12,178,546 B2
(45) Date of Patent: *Dec. 31, 2024

(54) METHODS AND SYSTEMS FOR MODIFYING ELECTRICAL CURRENTS IN NEURONAL CIRCUITS

(71) Applicants: The Regents of the University of California, Oakland, CA (US); The Brigham and Women's Hospital, Boston, MA (US)

(72) Inventors: Seung-Schik Yoo, Wellesley, MA (US); Alexander Bystritsky, Sherman Oaks, CA (US); Nathan McDannold, Jamaica Plain, MA (US); Ferenc A. Jolesz, Brookline, MA (US)

(73) Assignees: THE REGENTS OF THE UNIVERSITY OF CALIFORNIA, Oakland, CA (US); THE BRIGHAM AND WOMEN'S HOSPITAL, Boston, MA (US)

( * ) Notice: Subject to any disclaimer, the term of this patent is extended or adjusted under 35 U.S.C. 154(b) by 286 days.

This patent is subject to a terminal disclaimer.

(21) Appl. No.: 17/460,045

(22) Filed: Aug. 27, 2021

(65) Prior Publication Data

US 2021/0386293 A1 Dec. 16, 2021

Related U.S. Application Data

(63) Continuation of application No. 15/951,062, filed on Apr. 11, 2018, now Pat. No. 11,134,846, which is a
(Continued)

(51) Int. Cl.
*A61B 5/00* (2006.01)
*A61B 5/055* (2006.01)
(Continued)

(52) U.S. Cl.
CPC .......... *A61B 5/0036* (2018.08); *A61B 5/0042* (2013.01); *A61B 5/055* (2013.01);
(Continued)

(58) Field of Classification Search
None
See application file for complete search history.

(56) References Cited

U.S. PATENT DOCUMENTS

| 4,343,301 A | 8/1982 | Indech |
| 5,247,935 A | 9/1993 | Cline et al. |

(Continued)

FOREIGN PATENT DOCUMENTS

WO  WO2010/009141 A1  1/2010

OTHER PUBLICATIONS

Barlow et al., "The Risk of Seizures after Receipt of Whole-Cell Pertussis or Measles, Mumps, and Rubella Vaccine," *New England Journal of Medicine*, vol. 345, No. 9, pp. 656-661 (2001).
(Continued)

*Primary Examiner* — Jonathan Cwern
(74) *Attorney, Agent, or Firm* — MORGAN, LEWIS & BOCKIUS LLP

(57) ABSTRACT

A system comprises an ultrasound subsystem and a magnetic resonance imaging (MRI) subsystem. The ultrasound subsystem applies pulses of focused ultrasound having one or more parameters to an identified location in a subject that is to receive treatment. The parameters are determined in accordance with a magnetic resonance guided focused ultrasound (MRgFUS) treatment plan. The MRI subsystem acquires functional image data corresponding to the identified location concurrently with the applied pulses of focused ultrasound. The MRI subsystem obtains a reconstructed series of functional images of the subject using the functional image data. The functional images are indicative of a
(Continued)

first region within the identified location in which neuronal activity has been modified by the applied pulses. The system is configured to adjust one or more parameters of the MRgFUS treatment plan using the reconstructed series of functional images.

20 Claims, 5 Drawing Sheets

Related U.S. Application Data continuation of application No. 15/447,027, filed on Mar. 1, 2017, now abandoned, which is a continuation of application No. 12/707,197, filed on Feb. 17, 2010, now Pat. No. 9,592,409.

(51) Int. Cl.
 A61B 6/03 (2006.01)
 A61N 7/00 (2006.01)
 A61N 7/02 (2006.01)
 A61B 90/00 (2016.01)

(52) U.S. Cl.
 CPC ............... *A61B 6/037* (2013.01); *A61N 7/00* (2013.01); *A61N 7/02* (2013.01); *A61B 2090/374* (2016.02); *A61N 2007/0021* (2013.01); *A61N 2007/0026* (2013.01); *A61N 2007/0078* (2013.01)

(56) References Cited

U.S. PATENT DOCUMENTS

| | | | |
|---|---|---|---|
| 5,275,165 A | 1/1994 | Ettinger et al. | |
| 5,291,890 A | 3/1994 | Cline et al. | |
| 5,323,779 A | 6/1994 | Hardy et al. | |
| 5,476,438 A | 12/1995 | Edrich et al. | |
| 5,738,625 A | 4/1998 | Gluck | |
| 5,752,515 A | 5/1998 | Jolesz et al. | |
| 6,066,123 A * | 5/2000 | Li | A61K 9/0009 514/1.2 |
| 6,088,613 A | 7/2000 | Unger | |
| 6,094,598 A | 7/2000 | Elsberry et al. | |
| 6,148,225 A | 11/2000 | Kestler et al. | |
| 6,198,956 B1 | 3/2001 | Dunne | |
| 6,198,958 B1 | 3/2001 | Ives et al. | |
| 6,267,734 B1 | 7/2001 | Ishibashi et al. | |
| 6,348,793 B1 * | 2/2002 | Balloni | G16H 40/63 324/309 |
| 6,413,216 B1 | 7/2002 | Cain et al. | |
| 6,612,988 B2 | 9/2003 | Maor et al. | |
| 6,618,620 B1 * | 9/2003 | Freundlich | A61N 7/02 601/3 |
| 6,708,051 B1 | 3/2004 | Durousseau | |
| 7,283,861 B2 * | 10/2007 | Bystritsky | A61N 7/02 601/2 |
| 7,427,265 B1 | 9/2008 | Keilman et al. | |
| 7,505,807 B1 | 3/2009 | Kucharczyk et al. | |
| 8,086,296 B2 * | 12/2011 | Bystritsky | A61N 7/02 600/411 |
| 9,592,409 B2 * | 3/2017 | Yoo | A61N 7/02 |
| 11,134,846 B2 * | 10/2021 | Yoo | A61N 7/00 |
| 2002/0127230 A1 | 9/2002 | Chen | |
| 2002/0173697 A1 | 11/2002 | Lenhardt | |
| 2003/0204135 A1 | 10/2003 | Bystritsky | |
| 2004/0048795 A1 | 3/2004 | Ivanova et al. | |
| 2005/0240126 A1 | 10/2005 | Roley et al. | |
| 2006/0184069 A1 | 8/2006 | Vaitekunas | |
| 2007/0016031 A1 * | 1/2007 | Mourad | A61B 8/488 600/437 |
| 2007/0299370 A1 | 12/2007 | Bystritsky | |
| 2010/0026298 A1 | 2/2010 | Wald | |

OTHER PUBLICATIONS

Bachtold et al., "Focused Ultrasound Modifications of Neural Circuit Activity in a Mammalian Brain," *Ultrasound in Med. & Biol.*, vol. 24, No. 4, pp. 557-565 (1998).

Chapman et al., "Ultrasound-Induced Changes in Rates of Influx and Efflux of Potassium Ions in Rat Thymocytes in Vitro," *Ultrasound in Med. & Biol.*, vol. 6, pp. 47-49 (1974).

Clement et al., "A hemispher array for non-invasive brain therapy and surgery," *Physics in Medicine & Biology*, vol. 45, No. 12, pp. 3707-3719 (2000).

Colucci et al., "Focused Ultrasound Effects on Nerve Action Potential In Vitro," *Ultrasound in Med. & Biol.*, vol. 35, No. 10, pp. 1737-1747 (2009).

Fry et al., "Production of Reversible Changes in the Central Nervous System by Ultrasound," *Science*, vol. 127, No. 3289, pp. 83-84 (1958).

Fry, W. J., "Use of Intense Ultrasound in Neurological Research," *U.S. in Neurological Research*, pp. 143-147 (1957).

Gavrilov, L.R., "Use of focused ultrasound for stimulation of nerve structures," pp. 132-138 (1984).

Gavrilov et al., "Application of Focused Ultrasound for the Stimulation of Neural Structures," *Ultrasound in Med. & Biol.*, vol. 22, No. 2, pp. 179-192 (1996).

George et al., "Transcranial Magnetic Stimulation: A Neuropsychiatric Tool for the 21st Century," *Journal of Neuropsychiatry and Clinical Neuroscience*, vol. 8, No. 4, pp. 373-382 (1996).

Hertzberg et al., "Towards multifocal ultrasonic neural simulation: pattern generation algorithms," *Journal of Neural Engineering*, vol. 7 (2010).

Hill, C.R., "Ultrasonic Exposure Thresholds for Changes in Cells and Tissues," *The Journal of the Acoustical Society of America*, vol. 52, No. 2, Part 2, pp. 667-672 (1972).

Lele, P.P., "Effects of Ultrasonic Radiation on Peripheral Nerve with Observations on Local Heating," *Experimental Neurology*, vol. 8, pp. 47-83 (1963).

Mihran et al., "Temporally-Specific Modification of Myelinated Axon Excitability invitro Following a Single Ultrasound Pulse," *Ultrasound in Med. & Biol.* (1990).

Nyborg, W.L., "Mechanisms for Nonthermal Effects of Sound," *J. Acoust. Soc. Am.*, vol. 44, No. 5, pp. 1302-1309 (1968).

Rauch et al., "Clinical Neuroimaging in Psychiatry," *Harvard Review of Psychiatry*, vol. 2, No. 6, pp. 297-312 (1995).

Roth et al., "Deep Brain Stimulation in Neuropsychiatric Disorders," *Currnet Psychiatry Report*, vol. 3, No. 5, pp. 366-372 (2001).

The Regents of the University of California, International Search Report and Written Opinion, PCT/US2011/024914, Aug. 30, 2011, 6 pgs.

The Regents of the University of California, International Preliminary Report on Patentability, PCT/US2011/024914, Aug. 21, 2012, 4 pgs.

The Regents of the University of California, Invitation Pursuant to Rule 63(1), EP11745122.9, Mar. 6, 2017, 3 pgs.

The Regents of the University of California, Extended European Search Report, EP11745122.9, Jun. 26, 2017, 8 pgs.

The Regents of the University of California, Communication Pursuant to Rules 70(2) and 70a(2), EP11745122.9, Jul. 13, 2017, 1 pg.

Tsui et al., "In vitro effects of ultrasound with different energies on the conduction properties of neural tissue," *Ultrasonics*, vol. 43, pp. 560-565 (2005).

Tyler et al., "Remote Excitation of Neuronal Circuts Using Low-Intensity, Low-Frequency Ultrasound," *Ultrasonic Neurostimulation*, vol. 3, No. 10, pp. 1-11 (2008).

Tyler, W.J., "Noninvasive Neuromodulation with Ultrasound? A Continuum Mechanics Hypothesis," pp. 1-12 (2010).

Williams, A.R., "Release of serotonin from human platelets by acoustic microstreaming," *J. Acoust. Soc. Am.*, vol. 56, No. 5, pp. 1640-1643 (1974).

Schik-Yoo, Non-Final Office Action, U.S. Appl. No. 15/951,062, filed Nov. 24, 2020, 11 pgs.

\* cited by examiner

METHODS AND SYSTEMS FOR MODIFYING ELECTRICAL CURRENTS IN NEURONAL CIRCUITS

PRIORITY AND RELATED APPLICATIONS

This application is a continuation of U.S. patent application Ser. No. 15/951,062, filed on Apr. 11, 2018, entitled "Methods and Systems for Modifying Electrical Currents in Neuronal Circuits," now U.S. Pat. No. 11,134,846, issued on Sep. 15, 2021, which is a continuation of U.S. patent application Ser. No. 15/447,027, filed on Mar. 1, 2017, entitled "Methods for Modifying Electrical Currents in Neuronal Circuits," which is a continuation of U.S. patent application Ser. No. 12/707,197, filed on Feb. 17, 2010, entitled "Methods for Modifying Electrical Currents in Neuronal Circuits," now U.S. Pat. No. 9,592,409, issued on Mar. 14, 2017, all of which are hereby incorporated by reference in their entirety.

BACKGROUND OF THE INVENTION

The field of the invention is systems and methods for focused ultrasound ("FUS"). More particularly, the invention relates to methods for delivery of a focused ultrasonic pulse ("FUP") to different points of neuronal circuits within the brain under the guidance of an imaging system, such as magnetic resonance imaging ("MRI") system.

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

The MR signals acquired with an MRI system are signal samples of the subject of the examination in Fourier space, or what is often referred to in the art as "k-space". Each MR measurement cycle, or pulse sequence, typically samples a portion of k-space along a sampling trajectory characteristic of that pulse sequence. Most pulse sequences sample k-space in a raster scan-like pattern sometimes referred to as a "spin-warp", a "Fourier", a "rectilinear", or a "Cartesian" scan. The spin-warp scan technique employs a variable amplitude phase encoding magnetic field gradient pulse prior to the acquisition of MR spin-echo signals to phase encode spatial information in the direction of this gradient. In a two-dimensional implementation ("2DFT"), for example, spatial information is encoded in one direction by applying a phase encoding gradient, $G_y$, along that direction, and then a spin-echo signal is acquired in the presence of a readout magnetic field gradient, $G_x$, in a direction orthogonal to the phase encoding direction. The readout gradient present during the spin-echo acquisition encodes spatial information in the orthogonal direction. In a typical 2DFT pulse sequence, the magnitude of the phase encoding gradient pulse, $G_y$, is incremented, $\Delta G_y$, in the sequence of measurement cycles, or "views" that are acquired during the scan to produce a set of k-space MR data from which an entire image can be reconstructed.

An image is reconstructed from the acquired k-space data by transforming the k-space data set to an image space data set. There are many different methods for performing this task and the method used is often determined by the technique used to acquire the k-space data. With a Cartesian grid of k-space data that results from a 2D or 3D spin-warp acquisition, for example, the most common reconstruction method used is an inverse Fourier transformation ("2DFT" or "3DFT") along each of the 2 or 3 axes of the data set. With a radial k-space data set and its variations, the most common reconstruction method includes "regridding" the k-space samples to create a Cartesian grid of k-space samples and then perform a 2DFT or 3DFT on the regridded k-space data set. In the alternative, a radial k-space data set can also be transformed to Radon space by performing a 1 DFT of each radial projection view and then transforming the Radon space data set to image space by performing a filtered backprojection.

Functional magnetic resonance imaging ("fMRI") technology provides an approach to study neuronal activity. Conventional fMRI detects changes in cerebral blood volume, flow, and oxygenation that locally occur in association with increased neuronal activity induced by functional paradigms. An MRI system is used to acquire signals from the brain over a period of time. As the brain performs a task, these signals are modulated synchronously with task performance to reveal which regions of the brain are involved in performing the task. The series of fMRI time course images must be acquired at a rate that is high enough to see the changes in brain activity induced by the functional paradigm. In addition, because neuronal activity may occur at widely dispersed locations in the brain, a relatively large 3D volume or multi-slice volume must be acquired in each time frame.

With advances in brain imaging techniques, the pathophysiology of psychiatric and medical disorders began to be more and more related to the specific underlying neuronal circuits. Neuronal circuits are specific brain centers that are functionally and anatomically connected with each other. Usually, a circuit involves sub-cortical neuronal centers connected with cortex. While it is not entirely clear how these circuits operate, it is clear that they play a major role in multiple psychiatric, neurological, and medical conditions. For example, obsessive compulsive disorder ("OCD") and OCD spectrum disorders including impulse control disorders appear to be related to abnormalities in orbito-fronto-thalamic-striatum circuits. Likewise, panic disorder, social anxiety disorder, and panic spectrum disorders seem to be associated with the abnormal functioning of circuits involving orbital-frontal cortex, the amygdala, the cingulum and the hippocampus. Post-traumatic stress disorders seem to associate with abnormalities in prefrontal cortex, the amygdala, and the hippocampus. Psychotic disorders seem to have an association with prefrontal cortex-thalamic-striatum and occipital cortex circuits. Circuits involved in neurological conditions have also been identified. For example, Parkinson's disease, Huntington's disease, Tourette syndrome, and tick syndromes seem to have abnormalities in cortico-thalamic-straitum circuits. Chronic pain has association with cortico-thalamic circuits. Insomnia has association with temporal cortex-lymbic-cingulum circuits. Medical conditions seem to have connection with specific neurocircuitry. For example, obesity and stress are associated with temporal-hypothalamic circuits. For a simple review and description of the above circuits, see the studies described by D. L. Clark and N. N. Boutros in *The Brain and Behavior: An Introduction to Behavioral Anatomy*, 1999, and by S. L. Rauch, et al., in "Clinical Neuroimaging in Psychiatry," *Harvard Review of Psychiatry*, 1995; 2(6):297-312. In addition, substance abuse, including alcoholism and tobacco consumption, could be alleviated by modulating activation from the mesolimbic dopamine reward pathways.

Neuroimaging techniques exist that permit the assessment of rapid changes in activity of the brain, including functional MRI ("fMRI"), vector electroencephalography ("V-EEG"), and positron emission tomography ("PET"). These techniques, specifically fMRI, are capable of producing real time 3-dimensional maps of brain activity. These techniques merit scientists to study the neuronal circuits involved in pathology of different psychiatric or neurological conditions. However, the study process has been slowed by the absence of reliable activation of these circuits.

An orchestrated interplay among various neural circuitries in brain is responsible for normal neurocognitive behaviors and perception. Aberrant regional brain function, either caused by trauma or pathological conditions, results in a wide spectrum of neurological and neuropsychiatric disorders. Conventional pharmacological approaches have been based modulating the state of neurotransmission, such as, the use of neurotransmitter uptake inhibitors, or cellular excitability, such as, medications used in the seizure control. However, these methods generally lack anatomical specificity. Therefore, selective modification of a regional brain activity is desirable in order to study normal neurophysiology by altering the functional state of the specific component(s) in a neural circuitry-of-interest. The ability to modify regional brain function would also provide unprecedented opportunities in attempt to recover/suppress brain function.

Recently, a few novel methods of the treatment of mental and neurological disorders directed at neuronal circuits have been introduced. These include deep brain stimulation with implanted electrodes, which has been successfully used in OCD, Parkinson's disease, and epilepsy. Furthermore, brain surgery used in the treatment of OCD and depression has shown some success. See *New England Journal of Medicine*, 2001; 656-663, and R. M. Roth, et al., *Current Psychiatry Report*, 2001; 3(5):366-372. Because of their invasive nature and possible complications, these methods are reserved for the treatment resistant conditions where other treatments fail. However, the success of these treatments underlines the importance of specific neurocircuits in the pathophysiology of mental and neurological disorders. Furthermore, it underlines the importance of developing non-invasive methods of intervention at the neuronal circuit level.

Several invasive techniques have been developed with an aim of providing means of modulating regional brain function. For example, vagus nerve stimulation ("VNS"), believed to be mediated by modulation of release in neurotransmitters via electrical stimulation of the vagus nerves, has been used in treating epilepsy and depression. Similarly, deep brain stimulation ("DBS") provides targeted delivery of electrical stimulation by the surgical implantation of microelectrodes. The use of DBS has been implicated in treating essential tremor and Parkinson's disease via subthalamic nucleus ("STN") and the globus pallidus interna ("GPi"). These methods, while more anatomically specific, rely on surgical application of electrodes, thus accompany potential risk factors.

Recently it has been proposed that neuronal circuits can be assessed and modified non-invasively using transcranial magnetic stimulation ("TMS"). The signal from the brain after the TMS stimulation can be read using MRI. Exemplary methods for doing so have been described, for example, in U.S. Pat. No. 6,198,958, which is herein incorporated by reference in its entirety. The method and device proposed by that patent are currently being implemented in psychiatry and neurology for diagnostic and therapeutic purposes. See M. S. George, et al., Journal of Neuropsychiatry and Clinical Neuroscience (Fall 1996), Vol. 8, no. 4, pp. 373-382. The method, however, has several problems. For example, TMS does not stimulate deep brain centers because it is incapable of penetrating brain tissue deeper than 1-2 centimeters ("cm"). Also, TMS has a large area of focus, on the order of 1 cubic cm or more, which does not permit focused activation of a specific neuronal circuit. Also, there is a problem in using TMS together with fMRI, because TMS produces a magnetic signal that interferes with the magnetic field produced by MRI systems, which in turn negatively affects fMRI images.

Focused ultrasound has been used to modify electrical currents in neuronal tissue. This has been done by a combined application of a magnetic field and an ultrasonic field to neuronal and other tissue in the body. Previous methods propose that modification of electrical currents in neuronal tissue will come from the interaction of the two fields. For example, U.S. Pat. No. 4,343,301, describes generating high energy by intersecting two ultrasound beams within any single fixed point of the body, including the skull. While it is not proven that such an application of ultrasound would do anything except heat or destroy tissue, there is recent evidence that the application of focused ultrasound to brain slices, subjected to simultaneous electrical stimulation, can change the electrical currents in the slices. However, because two ultrasound beams cannot be focused within the skull, as a result of the complexity of bone density and bone structure, it is not possible to focus such a two-beam device in the brain tissue.

Some companies have produced ultrasonic devices that use multiple beams. See, for example, G. T. Clement, et al., *Physics in Medicine and Biology* (December 2000), Vol. 45, no. 12, pp. 3707-3719. By coordinating the amplitude and the phase of the ultrasound beams generated by multiple sources via computer multi-beam devices, algorithms can be developed to adjust the bone dispersion of the beam and focus the ultrasound within the brain tissue. These devices are to be used, for example, as ultrasonic knives within the brain for the destruction of tumors. However, they cannot be used to modify the electrical and electromagnetic currents within the brain circuits without harming the surrounding tissue.

It would therefore be desirable to provide a system and method for the non-invasive modification of neuronal activity. More particularly, it would be desirable to provide a system and method for the non-invasive modification of neuronal activity in a localized and reversible manner, without damage to the underlying tissue.

SUMMARY OF THE INVENTION

The present invention overcomes the aforementioned drawbacks by providing a method for localized, reversible, and noninvasive modification of neuronal circuitry with pulses of focused ultrasound ("FUS").

It is an aspect of the invention to provide a method for modifying electrical currents in a live neuronal circuit of a subject. The modification is accomplished by applying a FUS pulse ("FUP") under the guidance of an imaging system, such as a magnetic resonance imaging ("MRI") system, a vector-electroencephalograph ("V-EEG") system, or a positron emission tomography ("PET") system. The application of FUS pulses is generally via multiple ultrasound transducers that are housed in a cap worn by a patient. It is simultaneous with the use of the brain-imaging system. The application of different frequencies and phases of FUS pulses to the brain circuits will generate a signal that will be captured by the imaging device. At that time, changes in circuits are assessed. This permits an adjustment of the focus and location of the FUP, or the use of multiple focuses, to achieve the maximum modification of the neuronal circuit. The changes in the circuit are useful for research, diagnosis, and treatment.

It is another aspect of the invention to provide a method for treating psychiatric, neurological, and neuroendocrine disorders in a subject through application of FUS pulses. The treatment is accomplished by applying a FUP to a desired location in the subject, and the applied FUP uses a variation in frequency to disrupt or activate a tissue function. Monitoring is performed through an imaging system during the application of the FUS pulses.

It is yet another aspect of the invention to provide a method for diagnosing and treating specific psychiatric, neurological, and neuroendocrine conditions. Examples of such conditions include, but are not limited to, obsessive compulsive disorder and its spectrum, post traumatic stress disorder, depression, bipolar disorder, social anxiety disorder, psychotic disorders, panic disorder, ticks, chronic pain syndrome, insomnia, chronic fatigue syndrome, insomnia, stress and obesity, and other conditions apparent to one of ordinary skill in the art.

It is yet another aspect of the invention to provide a method for treating a mammal comprising the steps of administering a pharmaceutical medication to the mammal, assessing the pharmaceutical medication in the mammal with an imaging system to determine when the pharmaceutical medication distributes to or reaches a target location in the mammal, applying a focused ultrasound pulse (FUP) to the target location in the mammal to alter the pharmaceutical medication at the target location, and assessing the response from to the medication from the target location with an image from the imaging system during the application of the FUP. The alteration may cause a change in property of the pharmaceutical medication, such as for example, the chemical activity, composition and viscosity. In an embodiment, the alteration changes the pharmaceutical medication to an active form. Furthermore, the treatment of applying a FUP to a tissue of the mammal in combination with the administering of a pharmaceutical medication to the mammal and altering the pharmaceutical medication at a target location, all the while assessing the tissue activity and/or response through the imaging system, provides a novel manner of treating a number of disorders contemplated herein.

It is yet another aspect of the invention to provide a method for adjusting a magnetic resonance guided focused ultrasound ("MRgFUS") treatment plan. By way of example, functional MR images are acquired while neuronal activity is modified with pulsed focused ultrasound. These images are utilized to assess the focus of an ultrasound transducer to a treatment region in a subject, such as a region containing a tumor that is to be ablated. In this manner, the focus and other parameters of the MRgFUS treatment plan can be adjusted prior to the application of the FUS beam utilized to ablate the target region.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
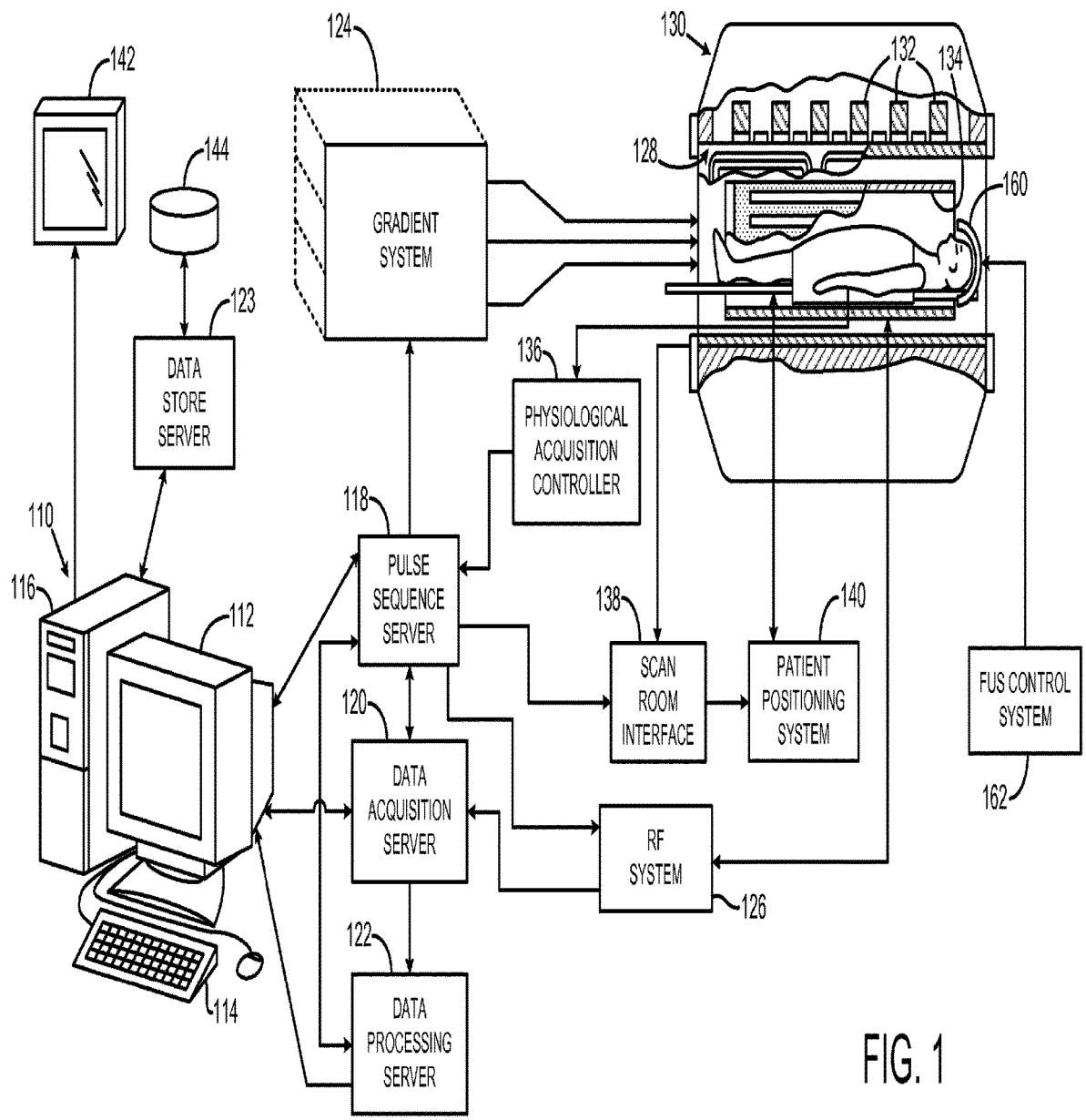
FIG. 1 is a block diagram of an exemplary magnetic resonance imaging ("MRI") system employed to practice MR guided focused ultrasound ("MRgFUS")

Referring particularly to FIG. 1, the preferred embodiment of the invention is employed in a magnetic resonance imaging ("MRI") system. The MRI system includes a workstation 110 having a display 112 and a keyboard 114. The workstation 110 includes a processor 116 that is a commercially available programmable machine running a commercially available operating system. The workstation 110 provides the operator interface that enables scan prescriptions to be entered into the MRI system. The workstation 110 is coupled to four servers: a pulse sequence server 118; a data acquisition server 120; a data processing server 122, and a data store server 123. The workstation 110 and each server 118, 120, 122 and 123 are connected to communicate with each other.

The pulse sequence server 118 functions in response to instructions downloaded from the workstation 110 to operate a gradient system 124 and a radiofrequency ("RF") system 126. Gradient waveforms necessary to perform the prescribed scan are produced and applied to the gradient system 124 that excites gradient coils in an assembly 128 to produce the magnetic field gradients $G_x$, $G_y$, and $G_z$ used for position encoding MR signals. The gradient coil assembly 128 forms part of a magnet assembly 130 that includes a polarizing magnet 132 and a whole-body RF coil 134.

RF excitation waveforms are applied to the RF coil 134 by the RF system 126 to perform the prescribed magnetic resonance pulse sequence. Responsive MR signals detected by the RF coil 134 or a separate local coil (not shown in FIG. 1) are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays (not shown in FIG. 1).

The RF system 126 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\theta = tan^{-1}\left(\frac{Q}{I}\right)$$

The pulse sequence server 118 also optionally receives patient data from a physiological acquisition controller 136. The controller 136 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 that receives signals from various sensors associated with the condition of the patient and the magnet system. It is also through the scan room interface circuit 138 that a patient positioning system 140 receives commands to move the patient to desired positions during the scan.

The digitized MR signal samples produced by the RF system 126 are received by the data acquisition server 120. The data acquisition server 120 operates in response to instructions downloaded from the workstation 110 to receive the real-time MR data and provide buffer storage such that no data is lost by data overrun. In some scans the data acquisition server 120 does little more than pass the acquired MR data to the data processor server 122. However, in scans that require information derived from acquired MR data to control the further performance of the scan, the data acquisition server 120 is programmed to produce such information and convey it to the pulse sequence server 118. For example, during prescans MR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process MR signals used to detect the arrival of contrast agent in a magnetic resonance angiography (MRA) scan. In all these examples the data acquisition server 120 acquires MR data and processes it in real-time to produce information that is used to control the scan.

The data processing server 122 receives MR data from the data acquisition server 120 and processes it in accordance with instructions downloaded from the workstation 110. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 122 are conveyed back to the workstation 110 where they are stored. Real-time images are stored in a data base memory cache (not shown) from which they may be output to operator display 112 or a display 142 that is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

An ultrasound transducer 160 is housed, for example, in a cap and includes multiple ultrasound transducer elements, for example, 300-1000 transducer elements. Transducer 160 is, for example, a multi-beam ultrasonic device that is controlled and coordinated with the MRI system via an FUS control system 162. The focal distance of the focal zone of the transducer 160 is controlled electronically by changing the phase and/or amplitude of the drive signals provided to the transducer 160, as described, for example, in U.S. Pat. No. 6,613,004. These drive signals are provided to the ultrasound transducer 160 by the FUS control system 162, which includes drive circuitry in communication with the ultrasound transducer 160. The FUS control system is also configured to drive the ultrasound transducer 160 in a prescribed manner by defining parameters such as, for example: acoustic intensity, tone-burst duration, total sonication duration, pulse repetition frequency, frequency of the applied ultrasound, and whether to operate the transducer 160 in a pulse or beam mode.

Figure 2:
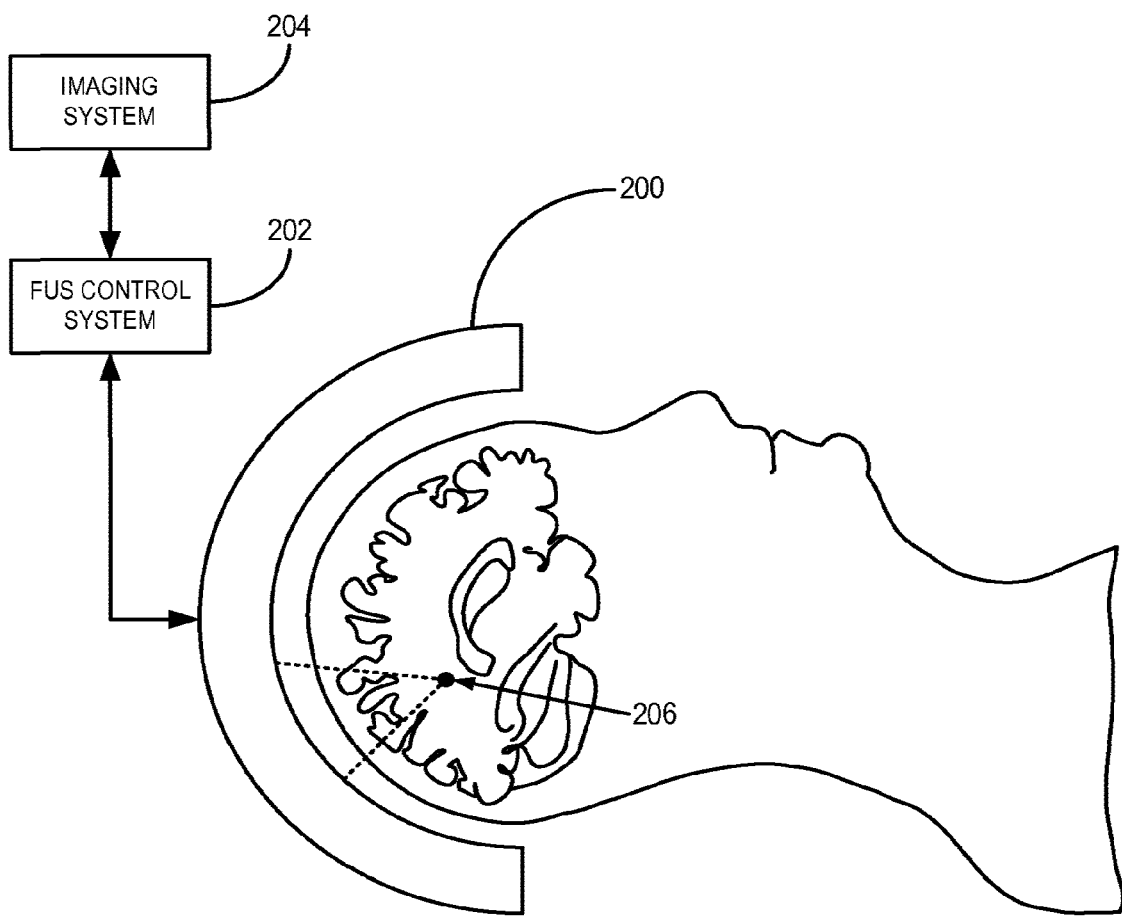
FIG. 2 is a block diagram of an exemplary ultrasound system employed when practicing the present invention.

FIG. 2 illustrates an exemplary stand-alone focused ultrasound ("FUS") system for use when practicing the present invention. Similar to the ultrasound system integrated with the MRI system of FIG. 1, the stand-alone system includes an ultrasound transducer 200 that is housed, for example, in a cap and which includes multiple ultrasound transducer elements, for example, 300-1000 transducer elements. The transducer 200 is, for example, a multi-beam ultrasonic device that is controlled by an FUS control system 202. In addition, the FUS control system is operable to coordinate the ultrasound transducer 200 with an imaging system 204, such as an MIll system as described above, or a vector-electroencephalography ("V-EEG") system or positron emission tomography ("PET") system. An exemplary multi-beam ultrasonic device is a so-called "ultrasound knife."

The focal distance of the focal zone of the transducer 200 is controlled electronically by changing the phase and/or amplitude of the drive signals provided to the transducer 200, as described, for example, in U.S. Pat. No. 6,613,004. These drive signals are provided to the ultrasound transducer 200 by the FUS control system 202, which includes drive circuitry in communication with the ultrasound transducer 200. The FUS control system is also configured to drive the ultrasound transducer 200 in a prescribed manner by defining parameters such as, for example: acoustic intensity, tone-burst duration, total sonication duration, pulse repetition frequency, frequency of the applied ultrasound, and whether to operate the transducer 200 in a pulse or beam mode.

The transducer 200 is regulated via the FUS control system 202, which is capable of focusing the ultrasound waves into a specific point 206. The cap and transducers are preferably made from a non-ferromagnetic material, a material that has a very low permeability and residual magnetism and hysteresis, such as copper. The use of a non-ferromagnetic material reduces magnetic field distortions that result in distortions of images acquired with an MIll system, thereby permitting the application of FUS pulses substantially contemporaneously with the use of an MIll system. By substantially contemporaneously, it is meant that one applies an FUS pulse within approximately 1 millisecond to 10 seconds before or after using the MIll system to image the subject.

As discussed above, the FUS control system 202 controls the parameters of the FUS produced by the ultrasound transducer 200, including focus, frequency, phase, and amplitude. Through user interaction with the control system 202, the transducer 200 is capable of producing a focused ultrasound pulse at a specific location 206 within the subject. Exemplary parameters for a FUS pulse ("FUP") include a focus that is 2 or more centimeters deep and 0.5-1000 mm in diameter. For example, the focus of the transducer 200 can be set by the control system 202 such that the focal point 206 is around 2-12 cm deep and 0.5-2 mm in diameter. The location 206 is identified, for example, using the imaging system 204. As mentioned above, the control system 202 is coordinated with the imaging system 204 in order to provide precise positioning and coordination of the focused ultrasound.

Figure 3:
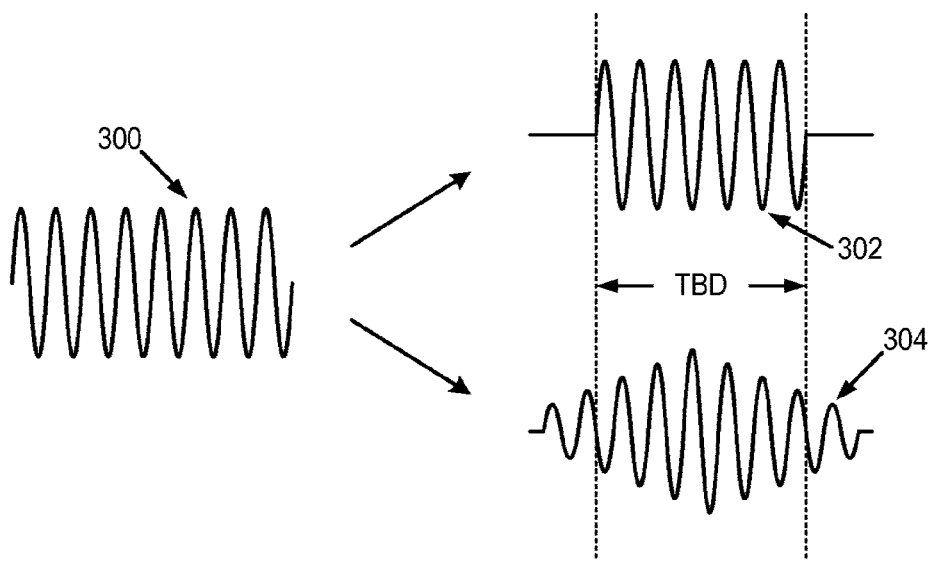
FIG. 3 is a graphic representation of an ultrasound driving signal and two corresponding focused ultrasound pulse ("FUP") driving signals.

The FUS control system 202 also controls the frequency, phase, and amplitude of the applied ultrasound energy. Referring now to FIG. 3, the driving parameters for the applied FUS pulses can be formed into pulses using two different pulse profiles. For example, using an input driving signal 300 having a given ultrasound energy frequency, such as 690 kilohertz ("kHz"), either a square wave pulse envelope or a one-half sine wave pulse envelope can be employed to modulate the input signal 300. Alternate exemplary ultrasound energy frequencies include those less than 1 MHz. Lower frequencies, such as those below 300 Hz, will decrease the firing of neurons in neuronal centers and, thereby, inhibit or disrupt neuronal activity. Conversely, higher frequencies, such as 500 Hz to 5 MHz, increase the firing of neurons in neuronal centers, thereby leading to an increase in neuronal activation. In either case, the FUS pulses modify physiological properties in the circuits. This happens both when the FUS pulses are applied to the neuronal centers in gray matter and to the white matter. The aforementioned modulation of the input driving signal 300 results in a square pulse 302 and a one-half sine wave pulse 304. The duration of these pulses is defined by their tone-burst duration ("TBD"), a quantity which is set by the FUS control system 202. Exemplary settings for TBD include 2-100 ms to provide increased neuronal activation, and 0.1-2 ms to provide decreased neuronal activation.

Figure 4:
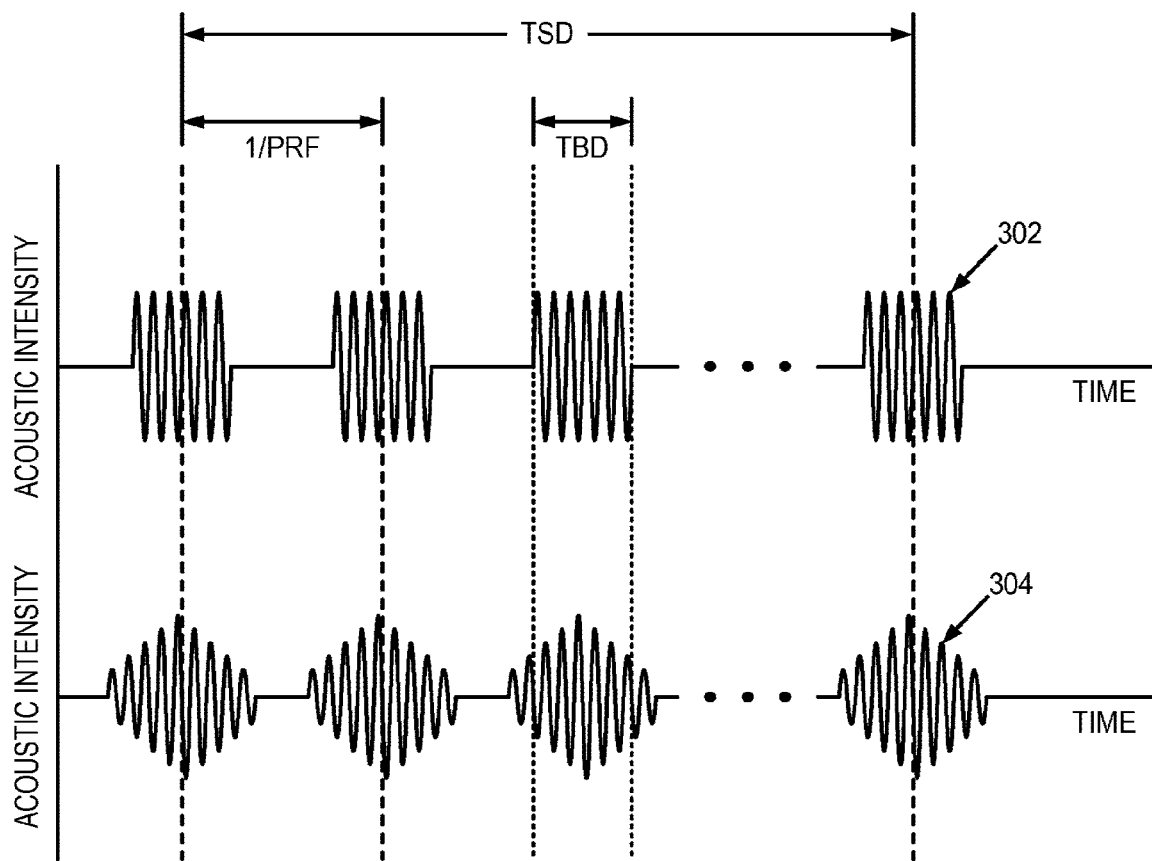
FIG. 4 is a graphic representation of a time series of FUPs, such as those produced by the driving signals of FIG. 3.

Referring now to FIG. 4, a time series of the exemplary square pulses 302 and one-half sine wave pulses 304 is shown. Each time series corresponds to a given sonication of the subject in accordance with the present invention. Thus, the duration of each sonication, referred to as the total sonication duration ("TSD"), defines each time series and is thereby selected by the FUS control system 202. Exemplary settings of TSD include 0.1-2 s to induce an increase in neuronal activation, and greater than 2 s to induce a decrease in neuronal activation. In fact, even when other parameters are configured to induce an increase in neuronal activation, a setting of TSD that is substantially greater than 2 s can elicit transient over-activity of the neural tissue, or bring the tissue to a refractory period in which there is reduced excitability followed by the neural activity. Moreover, when inducing a decrease in neuronal activity, a setting of TSD that is substantially greater than 2 s induces the suppression of the neuronal activity for an extended period, such as greater than 5 minutes, beyond the duration of the applied sonication.

The TBD of the one-half sine wave pulse 304 can be equated to the full-width at half-maximum ("FWHM") of the pulse 304, as is shown in FIG. 3. The duration of time that elapses between each pulse in a given time series, referred to as the pulse repetition period ("PRP"), is defined by the pulse repetition frequency ("PRF"), which is set by the FUS control system 202. The PRF is related to the PRP as follows:

$$PRP = \frac{1}{PRF}$$

Exemplary setting of PRF include 100-1000 Hz to provide decreased neuronal activation, and less than 100 Hz to provide increased neuronal activation. Each pulse is also defined by the corresponding acoustic intensity ("AI"), which is yet another parameter set by the FUS control system 202. The AI of each pulse is adjusted by modulating a voltage applied to the power amplifier that supplied the ultrasound transducer 200. It is important to note that AI determines the maximum peak acoustic pressure experienced by the tissue under sonication, and, accordingly, excessive pressure can lead to undesired tissue damage. Therefore, AI is kept at an appropriately minimal level while other sonication parameters are adjusted. Exemplary settings for AI include 10-350 watts per centimeter squared ("W/cm$^2$").

By way of example, to induce a decrease in neuronal activation in a selected cortical region, an ultrasound energy frequency of 690 KHz with an 8 cm focal depth is selected. The FUS pulses are applied with a TBD of 0.5 ms, a 10 ms PRP, which corresponds to a 100 Hz PRF, and an AI of 50 W/cm$^2$ for a TSD of 9 s. Such a set of exemplary settings results in robust activation in the selected cortical region, followed by the aforementioned temporary deactivation during the relative refractory period for more than 10 min.

By way of another example, excitation in the sensory-motor cortex is induced using FUS pulses having a TBD of 50-100 ms that are applied with a PRF of 10 Hz at different acoustic intensities in the range of 10-50 W/cm$^2$. More particularly, pulses with a 74 ms TBD and a 10 Hz PRF interval, which are administered for a TSD of 1 sec at an acoustic intensity of 25 W/cm$^2$, induce a robust and reproducible increase in measureable BOLD signal in fMRI images.

The mechanical index ("MI"), which is the estimated amount of maximum negative acoustic pressure, is an important criterion which determines the amount of mechanical damage to the tissue. The acoustic intensity of 50 W/cm$^2$ generated a pressure of around 1.34 megapascal ("MPa") at the focal spot. This corresponds to an MI value of 1.15, which is lower than the current FDA limit on soft tissue ultrasound imaging of 1.9. Thus, the applied sonication power employed in the foregoing example is within FDA limits and is also much less than the MI that causes blood-brain barrier disruption or cavitation.

Repeated application of the FUP to neuronal circuits causes long-term or permanent changes to the circuits. The modification of the circuits using FUP can be used for the treatment of psychiatric, neurological and neuroendocrine disorders. Examples of such diseases include, but are not limited to, obsessive compulsive disorder (and its spectrum), post traumatic stress disorder, depression, bipolar disorder, social anxiety disorder, psychotic disorders, panic disorder, ticks, chronic pain syndrome, insomnia, chronic fatigue syndrome, insomnia, stress, obesity, and other conditions apparent to one of ordinary skill in the art. This is done by repeated assessment and modification of changes in neuronal flow or field activity under the guidance of specific brain imaging techniques, such as fMRI, V-EEG, or PET.

Changes in activity within the neuronal circuits are determined by monitoring the changes in the brain image produced by the fMRI before the application of FUP and during and after the application of FUP. These changes are used to determine exactly where the FUP focus was in the brain and the functional connectivity between the focus and surrounding brain centers. The specific point may be confirmed using the addition of a computed tomography ("CT") scan, which provides information about bone density and structure of the skull and brain. The focus of the FUP may then be modified to direct it into a different point of the brain.

A single FUP may be applied to a single live neuronal circuit. Multiple FUPs may be applied to the same live neuronal circuit. Additionally, a single FUP may be applied to multiple live neuronal circuits, and multiple FUPs may be applied to multiple live neuronal circuits.

In one embodiment, there is provided a method of treating psychiatric, neurological and neuroendocrine disorders in a subject by applying a focused ultrasound pulse (FUP) to a tissue of the subject, and the applied FUP uses a variation in frequency to disrupt or activate a tissue function, and monitoring the tissue through a tissue image from an imaging system during the application of the FUP. The tissue can be that in the brain or another portion of the body. In specific embodiments, the tissue is that of a brain region such as the hypothalamus or medulla oblongata. The FUP application and the modulation can be monitored through a brain image from the imaging system. The application of FUP may also be applied to at least one other live neuronal circuit within the brain region concurrently.

Application of FUP to the hypothalamus, and more specifically to a hypothalamic nuclei, can modify the release of natural hormones and cause either an increase or decrease in release of a hypothalamic hormone. The hypothalamic hormone can be any of the following: corticotrophin-releasing hormone (CRH), dopamine, gonadotropin-releasing hormone, growth hormone-releasing hormone, melatonin, oxytocin, somatostatin, thyrotropin-releasing hormone, vasopressin, and mixtures thereof. The hypothalamic nuclei can be from the anterior nuclei, tuberal nuclei or posterior nuclei. The modification of release of natural hormones can help treat a number of disorders such as sexual disorder, menstrual disorder, diabetes, growth disorder, blood pressure disorder, thyroid disorder, skin disorder, and wake sleep cycle disorder. Gonadotropin-releasing hormone (GnRH), for example, can cause increases in testosterone and estrogen in males and females, which in turn can increase sexual desire, cause loss of weight, increase energy and decrease anxiety and depression. Increase in estrogen can also prevent osteoporosis, improve physiological and psychological symptoms associated with menstrual dysfunctions. Increase in growth hormone can help increase and improve the energy and height of people, as well as delay aging. Changes in Antidiuretic hormone (ADH) and Oxytocin can modify blood pressure and electrolyte imbalance. Thyrotropin-releasing hormone (TRH) regulates the release of thyroid hormone and modification of TRH levels can help in treatment of symptoms of hyper and hypo-thyroidism.

Neuroendocrine-immune interactions are regulated by CRH indirectly, through activation of a global stress response, and directly, through pro-inflammatory actions on peripheral immune functions. Neuroimmunological data have demonstrated that CRH activation of the sympathetic nervous system is essential in mediating the link between the brain and immune function. CRH is distributed in the brain and spinal cord, adrenal medulla, testes, ovaries, gastrointestinal tract, pancreas, myometrium, endometrium, placenta, and diverse inflammatory sites. Traditionally, hypothalamic CRH has been considered to act indirectly in an anti-inflammatory fashion, since the end product of the hypothalamic-pituitary-adrenal axis is cortisol, a well-known anti-inflammatory compound. Thus, activation of CRH will influence immunity and can treat immunological disorders without the negative side effects of external or synthetic hormonal therapy. A modification of the release of corticotrophin-releasing hormone wherein the hormone is increased may be used to treat a number of immunological disorders. It is also contemplated, however, that a decrease in CRH may help treat other disorders. For example, where the release of corticotrophin-releasing hormone is decreased, this may help treat opportunistic inflammations and fungal infections as well as beneficially affect some forms of cancer.

Application of FUP to the medulla oblongata can modulate an effect on the sympathetic or parasympathetic nervous system. This embodiment may be used to treat peripheral neuronal disorders such as bowel disorders, ulcers, inflammatory bowel syndrome disorder, irritable bowel syndrome disorder, arrhythmia, and high blood pressure.

The supra thalamic nuclei inputs into the pineal gland and can modify the level of melatonin, the hormone that regulates pigmentation of the skin and the sleep wake cycle. Modification of the pineal gland through FUP application to the supra thalamic nuclei may normalize sleep-wake cycle and treat some skin disorders such as excessive pigmentation.

Figure 5:
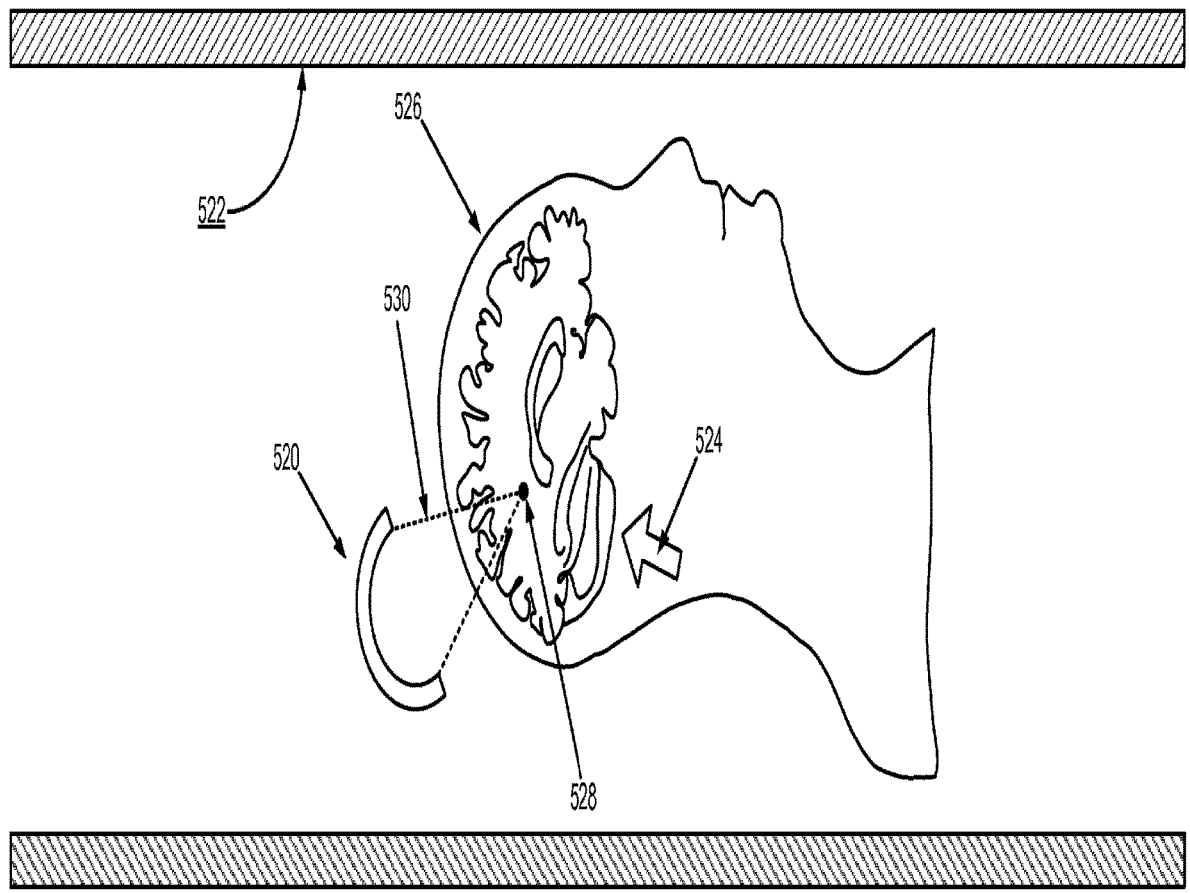
FIG. 5 illustrates an exemplary system in which a FUP device is employed in conjunction with an imaging system to alter an administered pharmaceutical medication to a subject.

FIG. 5 illustrates a system in accordance with an embodiment of the present invention in which the FUP device 520 is being used in conjunction with an imaging system 522 to alter an administered pharmaceutical medication 524 and assess a bodily reaction from the altered pharmaceutical medication. In this embodiment, a method of treatment is provided in which a pharmaceutical medication 524 is administered to the mammal 526, for example, through ingestion or injection. The pharmaceutical medication 524 is allowed to distribute to a target location 528 in the mammal 526, for example, a focal point in the brain. The target location can be the brain of the mammal or any other body tissue of the mammal.

Once it is determined that the medication 524 has distributed to the target location 528, a FUP 530 is applied to the target location 528 in the mammal 526 to alter the pharmaceutical medication 524. The alteration of medication during and after the application of the FUP 530 can be assessed with images from an imaging system 522. The imaging system may be selected from the group consisting of a functional magnetic resonance image (fMRI) system; a vector-electroencephalogram (V-EEG), and a positron emission tomography (PET). For example, in one embodiment, the pharmaceutical medication is administered to a subject in a non-toxic or non-active form. The medication is allowed to distribute and once the target location is reached, the FUP is applied to the focal point to alter the pharmaceutical medication. In embodiments, imaging techniques can be used to monitor and/or guide the medication as it reaches a target location or specific focal point, be it in the brain or another body tissue. One or more FUPs may be applied as needed and the alteration of the medication may be assessed through the imaging system. The frequency and phase of the FUP may also be changed to change the focus of any subsequently applied FUPs at the target location. Bodily reactions to the pharmaceutical medication after the applied FUP at the target location are assessed with an image from the imaging system.

Figure 6A:
FIG. 6A illustrates an exemplary neuronal activity response induced by the application of focused ultrasound in accordance with the present invention before the administration of a pharmaceutical medication, and as recorded by an exemplary electroencephalograph ("EEG") system.
Figure 6B:
FIG. 6B illustrates an exemplary neuronal activity response recorded by an EEG system and induced by the application of focused ultrasound in accordance with the present invention, and after the administration of a pharmaceutical medication that is ineffective at altering the subject's neuronal activity.
Figure 6C:
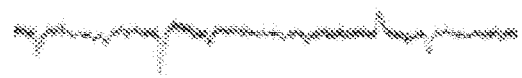
FIG. 6C illustrates an exemplary neuronal activity response recorded by an EEG system and induced by the application of focused ultrasound in accordance with the present invention, and after the administration of a pharmaceutical medication that is effective at altering the subject's neuronal activity.

By way of example, and referring particularly to FIG. 6A, an exemplary neuronal activity response induced by the application of focused ultrasound in accordance with the present invention, and before the administration of a pharmaceutical medication to the subject and as recorded by an exemplary electroencephalography ("EEG") system, is illustrated. After the pharmaceutical medication is administered to the subject, subsequent images indicative of the neuronal activity of the subject are acquired, as described above. If the pharmaceutical medication is ineffective at altering the subject's neuronal activity, substantially no change in the neuronal activity will be produced, as illustrated in FIG. 6B. On the other hand, when the pharmaceutical medication is effective at altering the subject's neuronal activity, this alteration will be apparent in the images acquired after the administration of the pharmaceutical medication. An exemplary alteration of this nature is illustrated in FIG. 6C. Thus, the method of the present invention is applicable to situations in which it is desired to determine the efficacy of a particular pharmaceutical medication, whether the assessment is directed to the particular medication employed, or the administered dose.

The alteration causes a change in property of the pharmaceutical medication—the property selected, for example, from the group consisting of chemical activity, composition and viscosity. In a particular embodiment, the alteration activates the pharmaceutical medication. By activating the medication with FUP once it is at a specific focal point in the body, specific medication that could not otherwise access the focal point without harmful effects can do so more safely. For example, an anti-cancer drug can be injected or orally ingested in non-active and non-toxic form. Subsequently, the drug can be activated once it is delivered precisely to the location of the brain tumor. FUP application is then used to alter the drug into an activate form, thus avoiding the toxicity from the drug in other parts of the body. The delivery and effect of the drug can be observed on the imaging. Similarly, a Parkinson patient can be administered a medication, such as a dopamine activating peptide, in an inactive form and subsequently activated using FUP near basal ganglia circuits causing effect only in that location. This manner of delivery will permit relieving the symptoms without suffering the usual side effects of dopaminergic drugs. In another example, the method may be used to deliver medication across the blood/brain barrier. Many substances cannot bypass the blood-brain barrier. Certain proteins such as liposomal proteins, however, can bypass the blood-brain barrier, so by covering a pharmaceutical medication with the protein, the medication can pass through the barrier. Once the medication has passed through the barrier, applied FUP can be used to destroy the liposomal protein. Moreover, this method can be used for drug delivery or activation within the brain or within any other tissue in the body.

Mechanical forces produced by frequency 300 Hz or higher can change properties of chemical substances within the FUP focus. These properties include, for example, a change in chemical activity, composition or viscosity. In particular, application of FUP at this frequency range can change the chemical structure by splitting the chemical structure, such as that of protein, RNA, DNA or peptides, into an active and inactive form. The change in the chemical properties or activity can be effected at the target location and can be assessed through imaging. The reaction of the tissue, neuronal centers or neuronal circuits to chemical substance activated by FUP will also be observed on the imaging.

The use of FUP in combination with fMRI or other imaging devices can provide a variety of diagnostic, research and therapeutic benefits. The invention can be used to create a functional map of the brain in response to modification of the neuronal circuits. It can also allow one to observe the functional connectivity within the brain of normal subjects as well as in the brain of the subjects suffering from various neurological conditions, such as the ones identified above. The present embodiments can also be used treat these conditions, and may be used concurrently with the pharmaceutical agents commonly prescribed for them. For example, the treatment of applying a FUP to a tissue of the mammal in combination with the administering of a pharmaceutical medication to the mammal and altering the pharmaceutical medication at a target location, all the while assessing the tissue activity and/or response through the imaging system, provides a novel manner of treating a number of disorders contemplated herein.

Development of the functional brain maps can significantly improve the understanding of the operation of the brain in normal subjects and in different diseased states. Unlike the use of transcranial magnetic stimulation (TMS), which can only read a brain tissue depth of about 1 to 2 cm, the FUP is able to reach brain tissue much deeper, 2 or more centimeters into the brain, for example, from about 2 to about 12 cm. Furthermore, the FUP can also produce a focus of energy that will be only from about 0.5 to about 2 mm in diameter, as opposed to about 2-3 cm. attainable by TMS.

The present embodiments can be used for the evaluation of the outcome of a variety of treatments. For example, the functional maps of the brain, such as those mapping functions of different areas of the brain after application of the FUP, may be constructed using fMRI before and after a particular treatment. If after the treatment the functional reactivity of a certain neuronal circuit becomes similar to that of normal controls, then that may be an indicator of the efficacy of a treatment. In the same way, the present embodiments can be used to determine when the activity of the certain neuronal areas reaches a specific level. The repeated application of FUP may modify the circuits in such a way that their functionality becomes the same as in normal subjects. Repeated application together with continuous fMRI monitoring may help to determine the most efficient, reliable and fast ways to achieve the normalization of neuronal structure and neuronal circuit function. As such, the present embodiments may make the FUP more efficient by determining the best phase, intensity and frequency of the pulse, as well as the best position of the focus or multiple focuses for diagnosis and treatment of the above-mentioned conditions.

For example, the functional maps of the brain could be created using fMRI before, during, and after a particular pharmaceutical is administered to a patient. If, after administration of the pharmaceutical, the functional reactivity of a certain neuronal circuit becomes similar to that of normal controls, then that may be an indicator of the efficacy of the agent.

As described above, the FUS system generates FUS pulses ("FUPs") that cause activation or deactivation of specific neuronal centers or circuits. The fMRI signal is modified in specific locations. This modification is captured and used to adjust the ultrasound transducers to achieve better focus, different position, or different influence on the neuronal circuit by modification of the ultrasonic parameters discussed above in detail.

The proposed FUS-mediated functional modulation can be used in conjunction with image-guided FUS ablation of brain tumors. For example, eloquent functional areas in close proximity to a brain tumor (the target of ablation) can be systematically modulated by the proposed method, and their functional representations can subsequently be monitored (either by real-time fMRI or cognitive tasks). The modulatory effect is only transient; therefore, the location of important functional areas that are affected by FUS sonication can be located, and thus avoided during subsequent FUS-mediated ablation procedures. Concurrently, the safety of the procedure can be increased significantly.

For example, an MRI system, such as the one in FIG. 1, is employed to perform a "rough" guidance of the ultrasound beam. After a focal location is identified with the MRI system, the FUS system is operated in accordance with the present invention to modulate the neuronal circuits in the region. This occurs while performing fMRI to elucidate those regions affected by the focus. A finer adjustment of the beam location can then be performed to ensure that substantially no healthy tissue is ablated during the FUS ablation procedure.

It has been described herein that FUS given in batches of pulses can increase and decrease the excitability of the neural tissue. A wide range of sonication ultrasound energy frequencies can be utilized while delivering the desired effects; however, considering the effects of transcranial absorption and reflection, the sonication frequency is typically less than 1 MHz. The suppressive effects of the present invention are applicable to both gray matter and white matter tissue, suggestive of selective and reversible disruption of white matter connectivity in neural circuitry.

The present invention has been described in terms of one or more preferred embodiments, and it should be appreciated that many equivalents, alternatives, variations, and modifications, aside from those expressly stated, are possible and within the scope of the invention.

What is claimed is:

1. A method for adjusting a magnetic resonance guided focused ultrasound (MRgFUS) treatment plan with a magnetic resonance imaging (MRI) system and an ultrasound system, comprising:
   identifying a location in a subject that is to receive treatment;
   applying, using the ultrasound system, focused ultrasonic pulses having one or more first parameters to the identified location in order to modulate a level of naturally occurring hormones of the subject at the location;
   concurrently with applying the pulses of focused ultrasound, acquiring with the MRI system functional image data corresponding to the identified location;
   obtaining a reconstructed series of functional images of the subject using the functional image data, the functional images indicative of a first region within the identified location in which neuronal activity has been modified by the applied pulses, wherein the first region is a region to be avoided in the treatment; and
   adjusting one or more parameters of the MRgFUS treatment plan using the reconstructed series of functional images, including:
      applying, using the ultrasound system, focused ultrasonic pulses having one or more second parameters to a second region within the identified location, the second region distinct from the first region, wherein the second region is a region to be treated in the treatment.

2. The method of claim 1, wherein the treatment is ablation of the second region.

3. The method of claim 1, wherein the modulation of the level of naturally occurring hormones is a transient modulation.

4. The method of claim 1, further comprising repeating the obtaining and adjusting such that neuronal circuits of the subject are modified by the repeated application of pulses of focused ultrasound so as to treat at least one of a psychiatric, neurological, and neuroendocrine disorder.

5. The method of claim 1, wherein the identified location comprises a location in the brain of the subject.

6. The method of claim 1, wherein identifying the location in the subject that is to receive treatment includes:
   acquiring, with the MRI system, image data from the subject;
   reconstructing an image of the subject from the acquired image data; and
   identifying the location in the subject using the reconstructed image.

7. The method of claim 1, wherein identifying the location in the subject that is to receive treatment includes:
   acquiring, with the ultrasound system, an image of the subject; and
   identifying the location in the subject using the acquired image.

8. The method of claim 1, wherein the one or more parameters include at least one of:
   a sonication period;
   a focused ultrasound acoustic intensity;

a focused ultrasound frequency;
a focal depth; and
a focal diameter.

9. The method of claim 1, wherein applying the focused ultrasonic pulses having one or more first parameters includes:
applying the pulses of focused ultrasound in a sequence according to a selected pulse repetition frequency (PRF) having a range of 100-1000 Hertz (Hz) in order to decrease neuronal activity, or at a selected PRF below 100 Hz in order to increase neuronal activity.

10. The method of claim 1, wherein the pulses of focused ultrasound having one or more first parameters are applied with an acoustic intensity having a range of 10-350 watts per centimeter squared ($W/cm^2$).

11. A system, comprising:
an ultrasound subsystem, configured to:
apply pulses of focused ultrasound having one or more parameters to an identified location in a subject that is to receive treatment in order to modulate a level of naturally occurring hormones of the subject at the location, wherein the one or more parameters are determined in accordance with a magnetic resonance guided focused ultrasound (MRgFUS) treatment plan; and
a magnetic resonance imaging (MRI) subsystem, configured to:
acquire functional image data corresponding to the identified location concurrently with the applied pulses of focused ultrasound; and
obtain a reconstructed series of functional images of the subject using the functional image data, the functional images indicative of a first region within the identified location in which neuronal activity has been modified by the applied pulses, wherein the first region is a region to be avoided in the treatment;
wherein the system is configured to adjust one or more parameters of the MRgFUS treatment plan using the reconstructed series of functional images, including applying, using the ultrasound subsystem, focused ultrasonic pulses having one or more second parameters to a second region within the identified location, the second region distinct from the first region, wherein the second region is a region to be treated in the treatment.

12. The system of claim 11, wherein the treatment is ablation of the second region.

13. The system of claim 11, wherein the modulation of the level of naturally occurring hormones is a transient modulation.

14. The system of claim 11, wherein the system is configured to repeat the obtaining and adjusting such that neuronal circuits of the subject are modified by the repeated application of pulses of focused ultrasound so as to treat at least one of a psychiatric, neurological, and neuroendocrine disorder.

15. The system of claim 11, wherein the identified location comprises a location in the brain of the subject.

16. The system of claim 11, wherein the system is further configured to:
acquire, with the MRI subsystem, image data from the subject;
reconstruct an image of the subject from the acquired image data; and
identify the location in the subject using the reconstructed image.

17. The system of claim 11, wherein the system is further configured to:
acquire, with the ultrasound subsystem, an image of the subject; and
identify the location in the subject using the acquired image.

18. The system of claim 11, wherein the one or more parameters include at least one of:
a sonication period;
a focused ultrasound acoustic intensity;
a focused ultrasound frequency;
a focal depth; and
a focal diameter.

19. The system of claim 11, wherein the ultrasound subsystem is configured to apply the pulses of focused ultrasound with an acoustic intensity having a range of 10-350 watts per centimeter squared ($W/cm^2$).

20. The system of claim 11, wherein the MRI subsystem is further configured to obtain a plurality of images indicative of neuronal activity that is induced by the applied pulses of focused ultrasound and altered in response to an administered pharmaceutical.

* * * * *